(12) United States Patent
Häcker (10) Patent No.: US 10,314,960 B2
(45) Date of Patent: Jun. 11, 2019

(54) BLOOD TREATMENT CASSETTE HAVING A STERILIZATION OPENING AND AN ASSOCIATED CLOSURE, AND BLOOD TREATMENT APPARATUS

(71) Applicant: FRESENIUS MEDICAL CARE DEUTSCHLAND GMBH, Bad Homburg (DE)

(72) Inventor: Jürgen Häcker, Neu-Anspach (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 68 days.

(21) Appl. No.: 15/122,143

(22) PCT Filed: Feb. 27, 2015

(86) PCT No.: PCT/EP2015/054163
§ 371 (c)(1),
(2) Date: Aug. 26, 2016

(87) PCT Pub. No.: WO2015/128474
PCT Pub. Date: Sep. 3, 2015

(65) Prior Publication Data
US 2016/0367742 A1 Dec. 22, 2016

(30) Foreign Application Priority Data

Feb. 27, 2014 (DE) .................. 10 2014 102 598

(51) Int. Cl.
| A61M 1/00 | (2006.01) |
| A61M 1/16 | (2006.01) |
| A61M 1/14 | (2006.01) |
| A61M 1/36 | (2006.01) |

(Continued)

(52) U.S. Cl.
CPC ............ *A61M 1/168* (2013.01); *A61L 2/0017* (2013.01); *A61L 2/24* (2013.01); *A61M 1/14* (2013.01);
(Continued)

(58) Field of Classification Search
CPC .............. A61M 1/168; A61M 2205/12; A61M 2205/128; A61L 2/24; A61L 2/0017; A61L 2202/22; A61L 2202/14
See application file for complete search history.

(56) References Cited

U.S. PATENT DOCUMENTS

| 4,817,800 A | 4/1989 | Williams et al. |
| 9,789,300 B2 | 10/2017 | Lauer |

(Continued)

FOREIGN PATENT DOCUMENTS

| CN | 102458505 | 5/2012 |
| CN | 103097717 | 5/2013 |

(Continued)

OTHER PUBLICATIONS

Description DE102009024469, english translation, accessed Mar. 26, 2018.*

(Continued)

Primary Examiner — Ariana Zimbouski
(74) Attorney, Agent, or Firm — Fish & Richardson P.C.

(57) ABSTRACT

A blood treatment cassette having a cassette body embodied as a hard part and, optionally, a film which is connected to the hard part and at least partially covers the hard part, wherein the hard part comprises at least one sterilization opening, and wherein the sterilization opening comprises a closure device. The invention also relates to a blood treatment apparatus for using the blood treatment cassette.

13 Claims, 5 Drawing Sheets

(51) Int. Cl.
*A61L 2/00* (2006.01)
*A61L 2/24* (2006.01)

(52) U.S. Cl.
CPC ........ *A61M 1/1686* (2013.01); *A61M 1/3621* (2013.01); *A61L 2202/14* (2013.01); *A61L 2202/22* (2013.01); *A61M 2205/12* (2013.01); *A61M 2205/121* (2013.01); *A61M 2205/128* (2013.01)

(56) References Cited

U.S. PATENT DOCUMENTS

| | | |
|---|---|---|
| 2009/0012450 A1 | 1/2009 | Shah et al. |
| 2010/0274168 A1 | 10/2010 | Gronau et al. |
| 2011/0064608 A1 | 3/2011 | Lee |
| 2011/0315611 A1* | 12/2011 | Fulkerson ........... A61M 1/3639 210/96.2 |
| 2013/0138037 A1 | 5/2013 | Lee et al. |

FOREIGN PATENT DOCUMENTS

| | | |
|---|---|---|
| DE | 10-2009-024469 A1 | 1/2011 |
| EP | 0292880 | 11/1988 |
| WO | 2010121819 | 10/2010 |
| WO | WO 2012/034734 | 3/2012 |
| WO | 2013-017235 A1 | 2/2013 |

OTHER PUBLICATIONS

International Search Report from PCT/EP2015/054163, dated Aug. 5, 2015.

* cited by examiner

BLOOD TREATMENT CASSETTE HAVING A STERILIZATION OPENING AND AN ASSOCIATED CLOSURE, AND BLOOD TREATMENT APPARATUS

CROSS REFERENCE TO RELATED APPLICATIONS

The present application is the national stage entry of International Patent Application No. PCT/EP2015/054163, filed on Feb. 27, 2015, and claims priority to Application No. DE 10 2014 102 598.9, filed in the Federal Republic of Germany on Feb. 27, 2014.

FIELD OF INVENTION

The present invention relates to a blood treatment cassette and a blood treatment apparatus.

BACKGROUND

Single-use systems are being increasingly used in the medical or laboratory technology as compact medical functional devices such as cassette systems or blood treatment cassettes in which liquids and gases, in particular medical fluids and blood, flow in channels and chambers. If they are provided for a single use, one speaks of disposable cassettes or one-way cassettes.

The blood treatment cassette is sterilized prior to use, for example by means of a sterilization fluid (steam, liquid, gas, etc.), which flows through the blood treatment cassette.

During steam sterilization of the blood treatment cassette, for example in a sterilization container of an autoclave, the air in the container is completely replaced by superheated steam in several cycles. The sterilization container having the blood treatment cassette (to be sterilized) therein is evacuated by vacuum pumps and then flushed with steam at elevated pressure. The superheated steam condenses on the surfaces of the blood treatment cassette which are to be sterilized. Depending on the size and design of the blood treatment cassette, this process is repeated according to need. It is important for the sterilizing effect that steam condenses on all surfaces of the blood treatment cassette. If the blood treatment cassette comprises voids or cavities having flexible elements, this can lead to undesirable deformations during the various phases of sterilization due to the large pressure changes. In particular, a blood treatment cassette having large cavities of a hard part of the blood treatment cassette (such as chambers or channels) which are covered by means of a film, is in this respect a particular challenge. The flow paths to the cavities comprise partly narrow areas (such as hydrophobic membranes or long, thin tubes) which have the effect that during pressure changes in the interior of the cavity there is a different prevailing pressure than that in the exterior. The additionally prevailing high temperature during sterilization may thus lead to irreversible deformation of the film.

SUMMARY

One object of the present invention is to provide a further blood treatment cassette with a device for improving the sterilizability of the blood treatment cassette. Further, a blood treatment apparatus is to be provided for the use of the blood treatment cassette.

According to the present invention a blood treatment cassette with a cassette body designed as a hard part is thus provided. The blood treatment cassette may optionally comprise a film. If a film is provided, then it is connected to the hard part and covers, during use, the hard part of the blood treatment cassette, at least partially.

The hard part or another section of the blood treatment cassette comprises at least one sterilization opening. This comprises at least one closure device, for example in the form of a sealing plug.

Further, a blood treatment apparatus is provided, which is configured or provided for connection with a blood treatment cassette according to the present invention. The blood treatment apparatus comprises at least one one-part or multi-part actuator provided, for example, in an actuator-sensor-mat or surface. The actuator is provided, designed, and/or configured to interact with the closure device of the blood treatment cassette in order to transfer the closure device from the first position into the second position.

In all of the following versions, the use of the expression may or may have", etc. is to be understood as a synonym to is preferably" or "preferably has", etc. and it is to explain an exemplary embodiment according to the present invention.

Whenever numerical words are mentioned herein, the skilled person understands this as an indication of a numerically lower limit. As long as it does not lead to any discernible contradiction for the skilled person, the skilled person, therefore, implicitly reads for example in the indication "one" at all times "at least one". This understanding is also encompassed by the present invention as well as the interpretation that, for example, "one" can alternatively be meant as "exactly one", as long as this is technically possible in the view of the skilled person.

The spatial information provided herein, such as "top", "bottom", etc. refers to the representation shown in the figures provided herein.

Embodiments according to the present invention may comprise one or more of the following features in any arbitrary combination.

In certain exemplary embodiments of the blood treatment cassette according to the present invention, the closure device is embodied so as to be, while it is connected with the sterilization opening, transferrable from a first position into a second position. Whereby, it is to be understood that the closure device in the first position allows a fluid exchange between the interior and an exterior of the blood treatment cassette by means of the sterilization opening (that is, through the latter), while it does not allow such an exchange of fluid in the second position. The first position is referred to herein as the open position, the second position as the closed position.

In some exemplary embodiments of the present invention, the closure device is embodied with a mechanism by means of which it can be maintained in the first and/or in the second position.

In certain exemplary embodiments of the present invention, the mechanism is a latching device or comprises one.

In some particular exemplary embodiments of the blood treatment cassette according to the present invention, the closure device is embodied so as it can be transferred into the second position also after completion of the sterilization of the blood treatment cassette, even if the blood treatment cassette is in a sheath or package which protects the sterility. In such embodiments, the closure device may be manually and/or for example, by means of a suitable mechanics automatically transferred into the second position.

In certain exemplary embodiments according to the present invention, the sterilization opening is provided or embodied in the hard part.

In some exemplary embodiments according to the present invention, the closure device comprises at least two sealing surface pairs of sealing elements or sections that are preferably separated from each other, respectively.

In certain exemplary embodiments according to the present invention, the blood treatment apparatus is connected to a blood treatment cassette according to the invention.

In some exemplary embodiments according to the present invention, the actuator is an immutable rising in or on an actuator-sensor mat, an actuator-sensor surface, or a door of the blood treatment apparatus. This rising is thereby immutable, for example, in its height, its rising above the level of its immediate surrounding, its geometry or the like.

In certain exemplary embodiments according to the present invention, the blood treatment apparatus comprises a device that is configured to change the actuator or any of its properties such as its height, its rising relative to the level of its immediate surrounding, its geometry and the like, and/or to transfer the closure device by means of the actuator from the first position into the second position.

In some exemplary embodiments according to the present invention, the blood treatment apparatus comprises a control device and at least one sensor. The blood treatment apparatus, for example, is configured by means of its control device or by means of another section, to determine by means of the sensor whether the closure device is in the first or the second position. Further, the blood treatment apparatus, for example again by means of the control device or by means of another section, is configured so as to prevent or interrupt a blood treatment by means of the blood treatment apparatus should it be ascertained that the closure device is not in the second position. Alternatively, it is configured so as to only allow a blood treatment if it is ascertained that the closure device is in the first position.

In certain exemplary embodiments according to the present invention, the sterilization opening serves only for the sterilization process.

In some exemplary embodiments according to the present invention, the sterilization opening is and remains closed after completion of the sterilization process, preferably irreversible or unless destructive forces are applied.

In some preferred embodiments according to the present invention, the sterilization opening is no single-needle sterile membrane and/or is no reception for a single-needle sterile membrane in the hard part.

In a further embodiment the cassette or its hard part comprises at least one single-needle sterile membrane and additionally a sterilization opening according to the present invention.

In some embodiments according to the present invention, the single-needle sterile membrane and the sterilization opening are different structures and separate from each other and may be provided in different sections of the cassette.

In some exemplary embodiments according to the present invention, combinations of sealing surface pairs are made of two relatively hard materials. In other exemplary embodiments according to the present invention, at least one of these surfaces is elastic.

In some exemplary embodiments according to the present invention, the actuator is configured to passively act on the closure device, in others, to actively act on the closure device. In a passive design the actuator may, for example, be embodied as a fixed machine-side cam or rising. In an active embodiment, the actuator may, for example, be embodied as a movable machine-side plunger.

In certain embodiments according to the present invention, the blood treatment cassette is a disposable or a single-use product.

In certain embodiments according to the present invention, the blood treatment cassette and/or the blood treatment device are configured for apheresis, for hemodialysis, for hemofiltration, hemodiafiltration, hemoultrafiltration, and the like.

Some or all embodiments according to the present invention may comprise one or more of the above mentioned or the following advantages.

One advantage of the present invention may include that there are no undesired deformations of the voids or cavities of the blood treatment cassette with flexible elements in spite of the great pressure changes during the individual phases of sterilization.

Another advantage of the present invention may also be that the additionally prevailing high temperature during sterilization which is caused, amongst others, by the prevailing pressure changes in the inner and outer area, does not lead to irreversible deformations, even in film cassettes and even in those film sections that cover large cavities such as chambers or channels of the hard part of the blood cassette body.

A further advantage of the present invention may be that a permanent deformation of the film, in case present, is prevented in that the pressure compensation between the inner area of the cavities and the outer area by means of the sterilization opening is accelerated.

In the following, the present invention shall be exemplary described while making reference to the drawings in which same reference numerals designate same or identical elements.

DETAILED DESCRIPTION

The standard arrows in the figures indicate the direction of the blood stream. The block arrows indicate the respective direction of the substituate stream.

Figure 1:
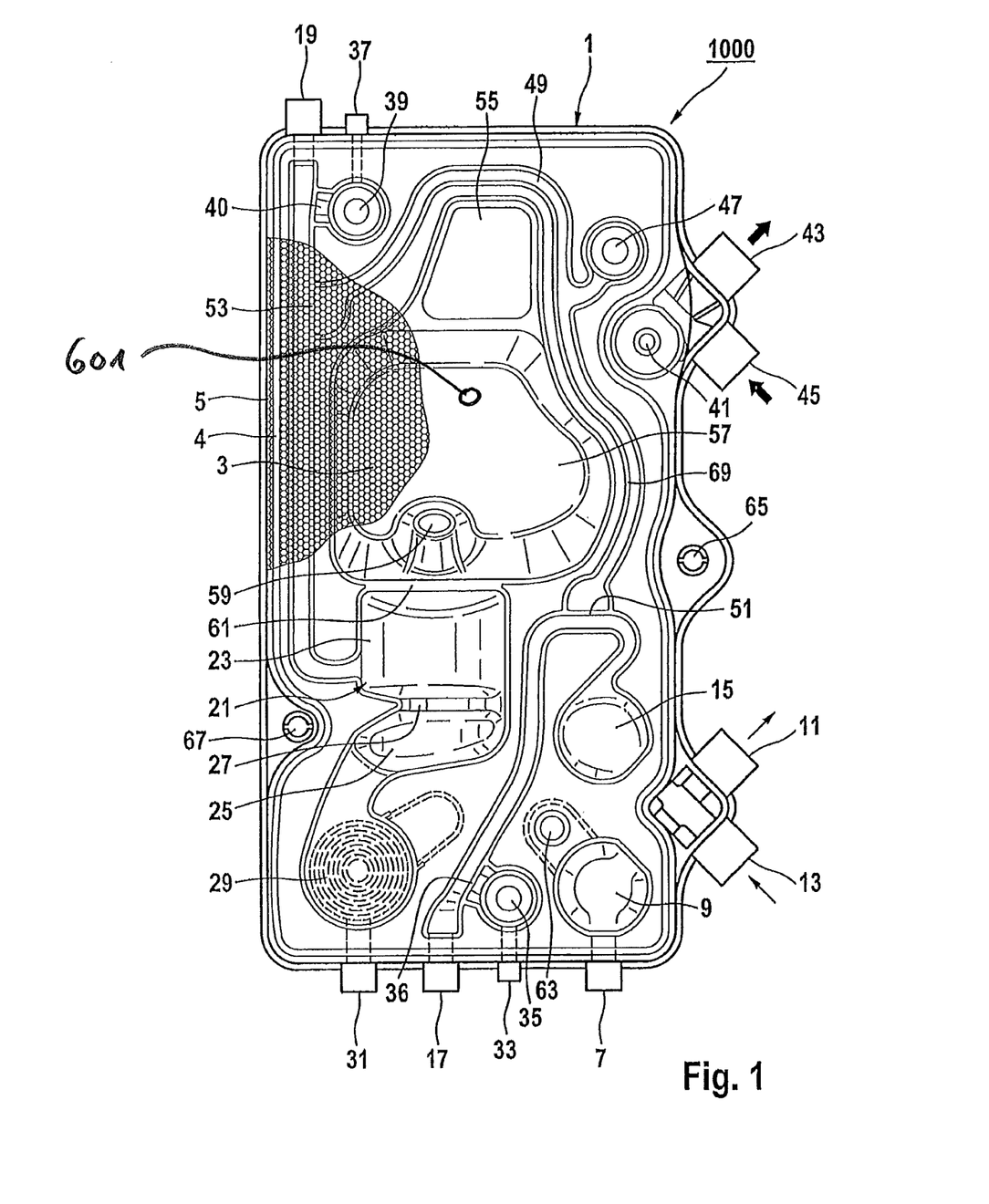
FIG. 1 shows a lateral view of a blood treatment cassette of the present invention provided, in accordance with a preferred embodiment, having a cover means on its front side.

FIG. 1 shows a lateral view of a blood treatment cassette 1000 according to the present invention which is provided with a cover means at the surface one looks upon in FIG. 1.

In the following, the blood treatment cassette 1000 according to the present invention is shortly referred to as cassette 1000.

The cassette 1000 comprises a hard part 1. As it is exemplarily shown in FIG. 1, the hard part 1 comprises chambers, passages and valves. As it is furthermore exemplarily shown in FIG. 1, the chambers, passages and valves are integrated into the hard part 1 or are at least partly formed by the hard part 1.

The cassette 1000 of FIG. 1 is provided at its front side with a cover means, here, for example, a film 3. The cover means may be welded in a flat manner, i.e., planarly, onto the hard part 1.

An embodiment involving a three-dimensional configuration of the weld and seal contour is also possible in accordance with the present invention.

The cover means may close the chambers and/or passages of the hard part 1 of the cassette 1000, namely, against a side facing away from the hard part 1 of the cover means and/or against the atmosphere.

As seen in FIG. 1, the film 3 rests on the hard part 1 of the cassette 1000 at a closed or peripheral sealing bar 4. The film 3 is welded with the hard part 1 of the cassette 1000 at a closed weld 5.

The closed or peripheral sealing bar 4 may alternatively be realized in an exposed manner.

The film 3 may be connected to the hard part 1 of the cassette 1000 at additional local welds (not shown). These may also be peripheral, i.e., closed in the sense of a terminating limitation similar to a ring, and/or dot-shaped.

The film 3 may locally be connected, e.g., welded, with the hard part 1 of the cassette 1000 in the form of dots or a line, in particular at the marginal zones of the liquid-conducting passages.

The film 3 may be connected to the hard part 1 of the cassette 1000 by laser welding. Here, it is advantageous if the local application of heat is carried out by using a light-absorbing component. The light-absorbing component may be part of the material of the film and/or of the hard part, or a layer disposed between film and hard part or above the film. The layer may be a film layer.

The cassette 1000 may be coupled to a blood treatment apparatus (not shown in FIG. 1) at least by its front side shown in FIG. 1. An exemplary technique for suitable coupling of a cassette 1000 to a coupling surface of a blood treatment apparatus is described in the patent applications (DE 10 2009 012 633.3) having the title "Vorrichtung zum Verbinden einer externen Funktionseinrichtung mit einer Anordnung, Anordnung aufweisend eine solche Vorrichtung und Verfahren zum Verbinden" [Device for connecting an external functional means to an arrangement, arrangement including a like apparatus, and connecting method] as filed with the German Patent and Trademark Office on Mar. 10, 2009, and (DE 10 2009 012 632.5) having the title "Abdichtungseinrichtung zum Abdichten eines Volumens einer medizinischen Behandlungsanordnung gegen ein weiteres Volumen sowie Anordnung und Verfahren" [Sealing means for sealing a volume of a medical treatment arrangement against another volume, as well as arrangement and method] also filed with the German Patent and Trademark Office on Mar. 10, 2009, the respective disclosures of which are herewith fully incorporated by way of reference.

The cassette 1000 may be coupled to a coupling surface of the blood treatment apparatus by the plane of the film 3 or through the intermediary of the latter.

The coupling surface of the blood treatment apparatus may be inclined to the rear, for instance at an upper portion thereof shown in FIG. 1, by 8 degrees against a vertical line extending from top to bottom in FIG. 1 (in the direction extending from the observer into the plane of drawing in FIG. 1).

The cassette 1000 comprises an arterial patient connection 7.

The cassette 1000 comprises a connector 11 for the exit of blood from the cassette 1000 as well as a connector 13 for the entry of blood into the cassette 1000.

The two connectors 11 and 13 are adapted to be connected to a pump tube segment or pump tube set of a blood pump.

The cassette 1000 further comprises a chamber 15 including a pressure measurement site for pressure measurement in the extracorporeal blood circuit upstream from the dialyzer ("pre-filter") or downstream from the pump ("post-pump"), respectively.

At the chamber 15 the pressure in the extracorporeal circuit upstream from the dialyzer may be measured across the film 3 or via the film 3.

The cassette 1000 comprises an arterial filter conduit 17 as well as a venous filter conduit 19.

The interior of the cassette 1000 comprises a venous blood chamber 21. The venous blood chamber 21 is subdivided into an upper space 23 and a lower space 25.

The upper space 23 of the venous blood chamber 21 may admit a laterally tangential inflow of blood. Here, blood may flow in laterally through the inlet (on the left side in FIG. 1) into the upper space 23 and spread out tangentially to the walls of the upper space 23. A laterally tangential inflow of blood may create a zone with a substantially or completely stable rotational flow of blood in the upper space 23 of the venous blood chamber 21.

The lower space 25 of the venous blood chamber 21 may represent a calming zone for the blood stream. Such a calming zone may possibly have substantially no rotational flow or no rotational flow of the blood present therein at all.

The venous blood chamber 21 is subdivided into the upper space 23 and the lower space 25 by a cross-sectional restriction 27 of the hard part 1 of the cassette 1000. The cross-sectional restriction 27 reduces the cross-section of the venous blood chamber 21 in its width and depth so as to result in a shoot or rapid downstream of which will flow with slower flow velocity. The upper space 23 and the lower space 25 are in fluid communication.

By means of such a construction, i.e., a subdivision of the venous blood chamber 21 into a zone with substantially or completely stable rotational flow of the blood and a calming zone for the blood stream, it is advantageously possible to achieve an efficient separation of air from the blood or fluid.

Walls of the upper space 23 and of the lower space 25 of the venous blood chamber 21 may suitably be adapted to an inclination of the upper portion of the cassette 1000 in FIG. 1 against the vertical, for example a rearward inclination of the upper part of the cassette 1000 shown in FIG. 1 by 8 degrees (into the plane of drawing). They may suitably have a rounded shape so as to advantageously represent a rheologically optimized contact surface for fluids passing through the venous blood chamber 21.

The cassette 1000 comprises a clot trap 29.

As a clot trap it is preferably possible to use a clot trap as disclosed in the patent application (DE 10 2009 024 495.6) having the title "Gerinnselfänger, externe Funktionseinrichtung, Blutkreislauf sowie Behandlungsvorrichtung" [Clot trap, external functional means, blood circuit and treatment apparatus] to the applicant of the present invention that was filed with the German Patent and Trademark Office on Jun.

10, 2009. The relevant disclosure thereof is herewith fully incorporated by way of reference.

At the clot trap 29, it is possible to measure the pressure in the extracorporeal circuit through the film 3 or across the film 3, i.e., in particular after passage through the dialyzer.

The cassette 1000 comprises a venous patient connection 31.

The cassette 1000 comprises an arterial heparin addition site 33. Here, it should be noted that the heparin addition site 33 (just like a venous heparin addition site 37) may also be suited and intended for adding other pharmacologically active agents than heparin, which are only in a preferred embodiment anti-coagulants or combinations of active agents. This should also be noted whenever heparin is mentioned supra or in the following in any kind of context.

The cassette 1000 comprises a check valve 35 of the arterial heparin addition site 33.

Exemplary check valves for the use as check valve 35 of the arterial heparin addition site 33 and also as further check valves of the cassette 1000 are disclosed in the patent application to the applicant of the present invention (DE 10 2009 024 469.7) having the title "Ventilvorrichtung, Ventileinsatz, externe Funktionseinrichtung, Behandlungsvorrichtung sowie Verfahren" [Valve device, valve insert, external functional means, treatment apparatus, and method] as filed with the German Patent and Trademark Office on Jun. 10, 2009, the relevant disclosure of which is herewith fully incorporated by way of reference.

The cassette 1000 comprises an arterial heparin addition valve 36. By means of the arterial heparin addition valve 36 the addition of heparin into the arterial filter conduit 17 may be controlled or regulated.

The arterial heparin addition valve 36 may be configured as a so-called phantom valve.

The expression "phantom valve" used herein designates an element having an actor surface (in the present case, for example, an actor membrane) that may be reached by means of an actor that may adopt the function of a valve.

The actor membrane can be made to move, dilate or curve etc. in one direction by applying a force on it, e.g., a pressing force. As a result of its movement or dilatation, the actor membrane may come into contact with an element such as a sealing device, e.g., a bar, or move away from the latter. The actor membrane may thus, for example, effect or enhance or terminate or reduce a sealing effect.

When the force acting on the actor membrane is ceased to apply or is released, the latter may return, for example, to a basic position, e.g., a non-curved condition.

A phantom valve for use as an arterial heparin addition valve 36 as well as further phantom valves of the cassette 1000 may be configured with or from a bar portion of a passage at the hard part 1 of the cassette 1000 and a portion of the film 3 contacting or facing the bar portion.

Phantom valves may be operated through actors of the blood treatment apparatus.

In order to close a phantom valve, the portion of the film 3 may be pressed onto the bar portion. In order to open the phantom valve, the portion of the film 3 may again be raised from the bar portion.

Further examples and/or embodiments for phantom valves may be found in the patent application (DE 10 2009 012 632.5) having the title "Abdichtungseinrichtung zum Abdichten eines Volumens einer medizinischen Behandlungsanordnung gegen ein weiteres Volumen sowie Anordnung and Verfahren" [Sealing device for sealing a volume of a medical treatment arrangement against another volume, as well as arrangement and method], as filed with the German Patent and Trademark Office on Mar. 10, 2009 by the present applicant besides the patent application (DE 100 53 441 A1) and the patent application (DE 102 24 750 A1).

The relevant disclosures thereof are herewith fully incorporated by way of reference.

The cassette 1000 comprises a venous heparin addition site 37. The venous heparin addition site 37 may be configured as a Luer-connector.

The cassette 1000 comprises a check valve 39 of the venous heparin addition site 37.

The cassette 1000 comprises a venous heparin addition valve 40. With the aid of the venous heparin addition valve 40 the addition of heparin into the venous filter conduit 19 may be controlled or regulated.

The cassette 1000 comprises a substitute addition site 41 or a substitute connector, respectively.

The substitute addition site 41 may be a connection means as it is described in the patent application (DE 10 2009 024 575.8) to the present applicant having the title "Verbindungseinrichtung and Verfahren zum Verbinden wenigstens zweier fluidführender medizintechnischer Systeme, sowie medizintechnische Vorrichtung" [Connection means and method for connecting at least two fluid-conducting medical-technical systems, as well as a medical-technical apparatus] as filed with the German Patent and Trademark Office on Jun. 10, 2009 by the present applicant. The relevant disclosure thereof is herewith fully incorporated by way of reference.

The substitute addition site 41 may be provided with a touch-protection element (not shown). The substitute addition site 41 may be provided with a drip-protection element (not shown). The drip-protection element may be realized through an integrated closure sleeve. The drip-protection element may prevent residues of substitute and/or blood from dripping out when the cassette 1000 is released and subsequently removed from the blood treatment apparatus.

The drip-protection element may be realized to be removable. It may be configured as a hood or lid.

The substitute addition site 41 or some other portion of the cassette 1000 may moreover provide a tamper protection, by which of which the user recognizes readily, or at one glance, whether the cassette 1000 has already been used. This tamper protection may be realized by means of the touch-protection element, the closure sleeve, or some other structure. Preferably, the corresponding structure may recognizably change its position inside or relative to the cassette 1000. Preferably it may change its shape.

Moreover, the substitute addition site 41 or some other portion of the cassette 1000 may provide a protection against reuse. In a preferred manner, the cassette 1000 is made unusable by means of a closure sleeve—preferably in an irreversible manner—with respect to an attempted reuse. If the cassette 1000 should nevertheless be used again, sensors of the blood treatment apparatus do not measure the signal characteristics that would be measured during use of a new cassette. This may be due to the fact that liquid can not enter into the cassette 1000 or into the substitute addition site 41, or at least not in a sufficient or usual quantity. The control unit of the blood treatment apparatus may recognize this. A warning may be triggered.

As a tamper protection or a protection against reuse, it is preferably possible to use a tamper protection or protection against reuse as disclosed by the applicant of the present invention in the patent application (DE 10 2009 024 575.8) having the title "Verbindungseinrichtung and Verfahren zum Verbinden wenigstens zweier fluidführender medizintechnischer Systeme, sowie medizintechnische Vorrichtung"

[Connection means and method for connecting at least two fluid-conducting medical-technical systems, as well as a medical-technical apparatus] that was filed with the German Patent and Trademark Office on Jun. 10, 2009. The relevant disclosure thereof is herewith fully incorporated by way of reference.

The cassette comprises a connector 43 for the exit of substituate from the cassette 1000 as well as a connector 45 for the entry of substituate into the cassette 1000.

The connectors 43 and 45 are adapted to be connected to a pump tube segment or a pump tube set of a substituate pump.

The cassette 1000 comprises a check valve 47 for the addition of substituate.

Substituate may be introduced into a substituate conduit 49 by operating the check valve 47.

The cassette 1000 comprises a pre-dilution addition valve 51. The pre-dilution addition valve 51 may be configured as a phantom valve.

The cassette 1000 comprises a post-dilution addition valve 53. The post-dilution addition valve 53 may be configured as a phantom valve.

The cassette 1000 comprises a single-needle sterile membrane 55.

The cassette 1000 comprises a single-needle chamber 57. In FIG. 1, the single-needle chamber 57 is arranged above the venous blood chamber 21.

Inside the single-needle chamber 57 an optional blood surge redirection element 59 is arranged. The blood surge redirection element 59 may serve for decelerating a blood surge and/or cancelling its impulse.

A connection to an inside of the single-needle chamber 57 may be provided by means of a connection means as disclosed by the applicant of the present invention in the patent application (DE 10 2009 024 467.0) having the title "Einrichtung sowie externe Funktionseinrichtung und Behandlungsvorrichtung zum Behandeln von medizinischen Fluiden" [Device and external functional means and treatment apparatus for the treatment of medical fluids] that was filed with the German Patent and Trademark Office on Jun. 10, 2009. The relevant disclosure thereof is herewith fully incorporated by way of reference.

The cassette 1000 comprises a single-needle blood valve 61. The single-needle blood valve 61 may be configured as a phantom valve.

The cassette 1000 comprises an evacuation site 63. The evacuation site 63 may serve for vacuum coupling of the cassette 1000 to the blood treatment apparatus as is described, for example, in the patent application (DE 10 2007 042 964 A1) having the title "Vorrichtung und Verfahren zur Behandlung einer medizinischen Flüssigkeit" [Apparatus and method for treating a medical liquid] that was filed with the German Patent and Trademark Office on 10 Sep. 2007. The relevant disclosure thereof is herewith fully incorporated by way of reference.

The cassette 1000 comprises a primary alignment center 65. The primary alignment center 65 may advantageously serve for aligning and/or latching of the cassette 1000 on the blood treatment apparatus.

The cassette 1000 comprises a secondary alignment site 67. The secondary alignment site 67 may serve for aligning and/or latching of the cassette 1000 on the blood treatment apparatus.

The cassette 1000 is filled with gas (e.g., sterile air) prior to beginning priming. During priming of the extracorporeal blood circuit this gas filling has to be displaced. Insofar, a blood treatment cassette generally represents a particular challenge as there are both rising and falling conduits and moreover chambers in which no "air nests" must remain. For this purpose, the present cassette 1000 is provided with special construction features:

The chamber 15 for measuring the arterial pressure is constructed such that the entire air may rise into a pump tube segment (e.g., into the pump tube segment 90). Advantageously, there are no dead spaces present. Air rising by itself from the arterial pressure measurement chamber into the pump tube segment of the blood pump is forcibly conveyed through the pump tube segment from the engagement site of the blood pump (e.g., by the rollers of a roller pump). As soon as the pump ceases to exert an influence (for instance due to disengaging rollers), the air rises by itself into the cassette 1000 in the conveying direction.

The venous recirculation conduit (or a venous portion 93 of the extracorporeal blood circuit) is a downward conduit. Starting from a particular herein prevailing volume flow (e.g., 200 ml/min in the case of the cassette 1000 shown in FIG. 1), air bubbles in the blood are "entrained" even against gravity. This effect is made benefit from in the downward conduits. The conduit cross-sections of the downward conduits are designed with such a small size such that a forcible conveyance of the air bubbles even against gravity is successful due to the flow velocity.

In the venous blood chamber 21 large cross-sections are provided, such that air bubbles may reliably rise there against the main direction of flow due to the slower or lower flow velocities prevailing there.

Further constructive features of the cassette 1000 are as follows:

The phantom valves 40, 51 and 53 are physically oriented such that blood (which has a higher density than water or substituate, etc.) can hardly penetrate "upward" or "sideways" into opened phantom valves while the cassette 1000 is operated with blood, for the latter descends as compared to the lighter water. Such an advantageous orientation is realized with the aid of the phantom valves 40, 51, and 53. The valve 36, on the other hand, does not imply such a requirement, i.e., the orientation is not crucial there.

For the same reason, the conduit passage (stub passage) below the check valve 47 for adding substituate is constructed in a rising manner. In the event of a malfunction of the pre- and/or post-dilution valves 51 and 53 and a resulting bypass flow of blood, blood can not rise into the substituate conduit 49 any more. The blood will rather flow past the opening of the corresponding stub conduit.

The inclination of the cassette 1000 preferably is from 5 degrees to 11 degrees, in a particularly preferred manner (8 degrees) as already mentioned above.

Reference numeral 601 denotes a sterilization opening. It connects an exterior of the cassette 1000 with an interior thereof. The sterilization opening 601 may be arranged, for example, to connect an interior of the single-needle chamber 57 to the exterior. It may be located in the single-needle chamber 57.

Figure 2:
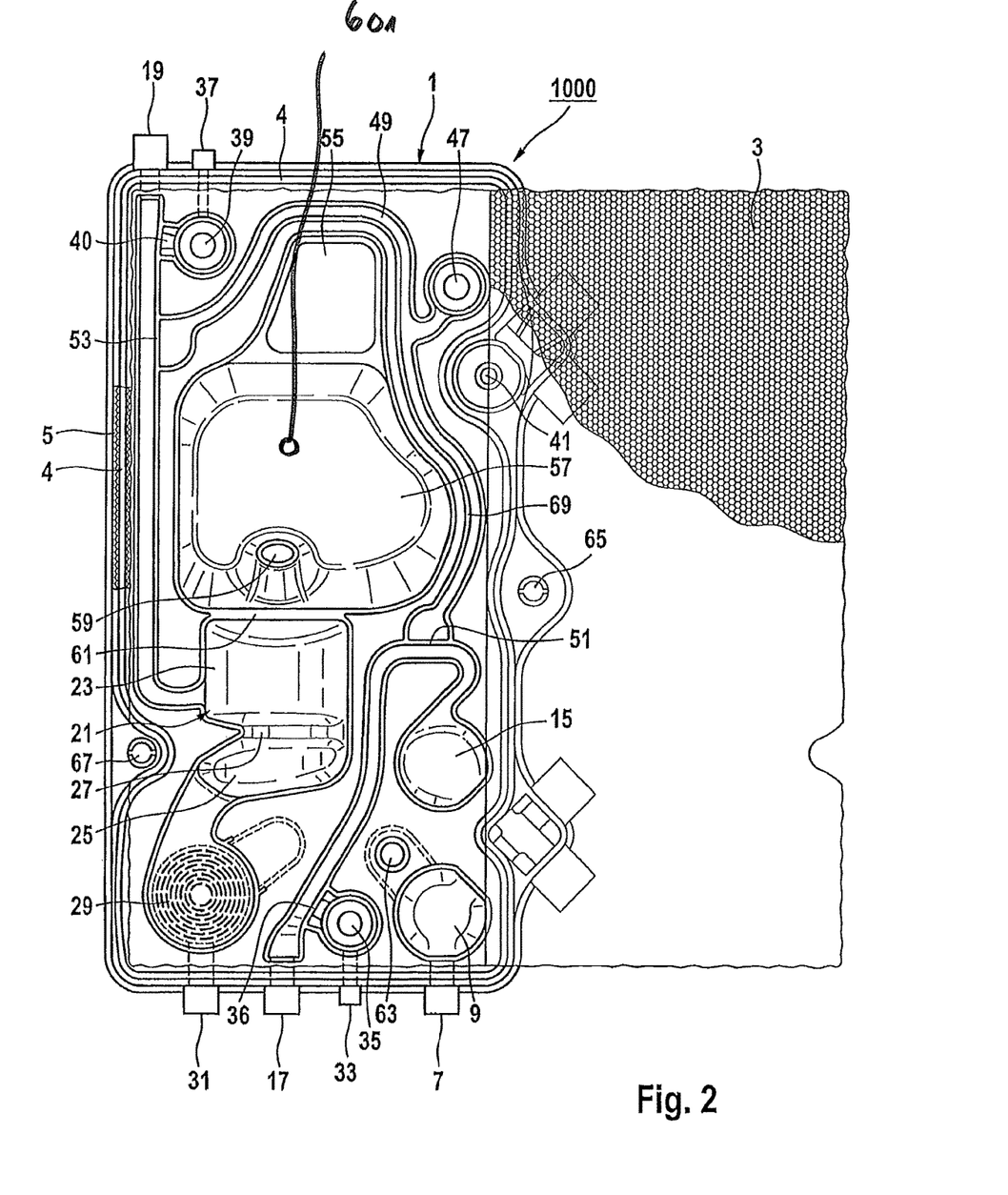
FIG. 2 shows the blood treatment cassette of FIG. 1 with the cover means swung-open following destructive cutting.

FIG. 2 shows the cassette 1000 of FIG. 1, wherein the film 3 is recognized to be cut open destructively at the left-hand margin of the cassette 1000 as well as at the top and bottom and swung open to the right for better illustration.

As is shown in FIG. 2, the film 3 comprises a surface texture.

FIG. 2 shows the elements inside the cassette 1000 which are visible in more detail after having cut open the film 3.

In order to avoid repetitions, reference is made to the configurations of the individual elements discussed in the description of FIG. 1.

Here it is clearly seen that the cassette 1000 comprises a sealing bar 69. The sealing bar 69 may be employed, for example, for realizing the pre-dilution addition valve 51.

Figure 3:
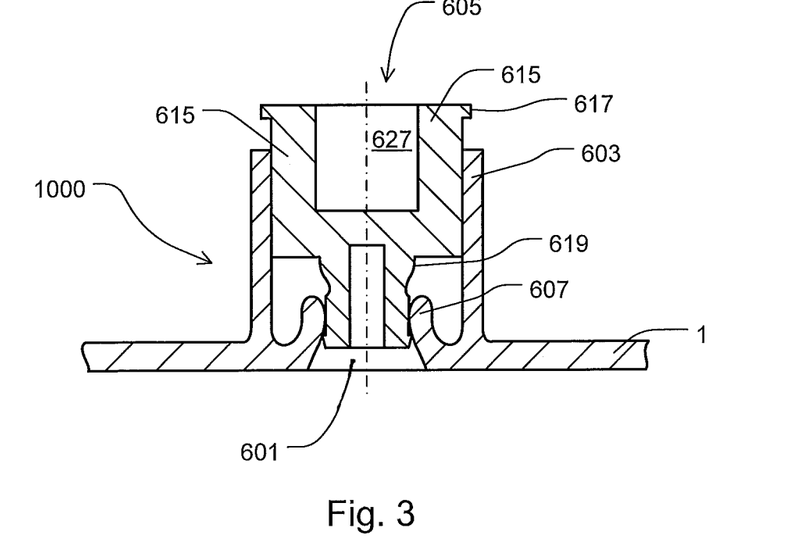
FIG. 3 shows in a schematically simplified manner a section of the hard part of the blood treatment cassette according to the invention, also referred to herein as a cassette, with the sterilization opening and a herein provided closure device in the first open position in longitudinal section.

FIG. 3 shows in a schematically simplified manner a section of the hard part 1 of the blood treatment cassette 1000 according to the present invention, also referred to herein as a cassette 1000, in longitudinal section.

The hard part 1 comprises, as purely optional, a cylindrical section 603 which encloses the sterilization opening 601 connected in a cylinder form to the latter and/or extends it in a fluid-tight manner.

In the cylinder section 603, to be seen in FIG. 3, a closure device 605 is inserted. The closure device 605 is designed to be able to seal the sterilization opening 601 depending on the position that the closure device 605 is occupying relative to the sterilization opening 601 and/or depending on the deformation that the closure device 605 is taking on.

In FIG. 3, the closure device 605 occupies a first position. The sterilization opening 601 is therefore not closed in a fluid-tight manner by the closure device 605, which is embodied, here purely by way of example, as a sealing plug. Rather, it remains open, or at least partially open, as the closure device 605 also in a lower (relative to the illustration of FIG. 5) section 605*a* that is connected to an upper section of the closure device 605, tapered (i.e., comprising a smaller diameter) comprises struts 605*b* (here by way of example four pieces; a different number of struts 605*b* is also encompassed by the present invention), see FIG. 5. Fluid can penetrate through them or past them into the interior of the cassette 1000. In the position shown in FIG. 4, it is different notwithstanding this.

The closure device 605, as shown in FIG. 3, may, purely by way of example, comprise a latching device 607. The latter is provided to hold the closure device 605 in the second closed position in which fluid can not penetrate through the sterilization opening 601 into the cassette 1000, as soon as a latching has taken place.

In FIG. 3, the closure device 605 is, however, not latched by means of the latching device 607, and thus the sterilization opening 601 is shown in the first open position.

Figure 4:
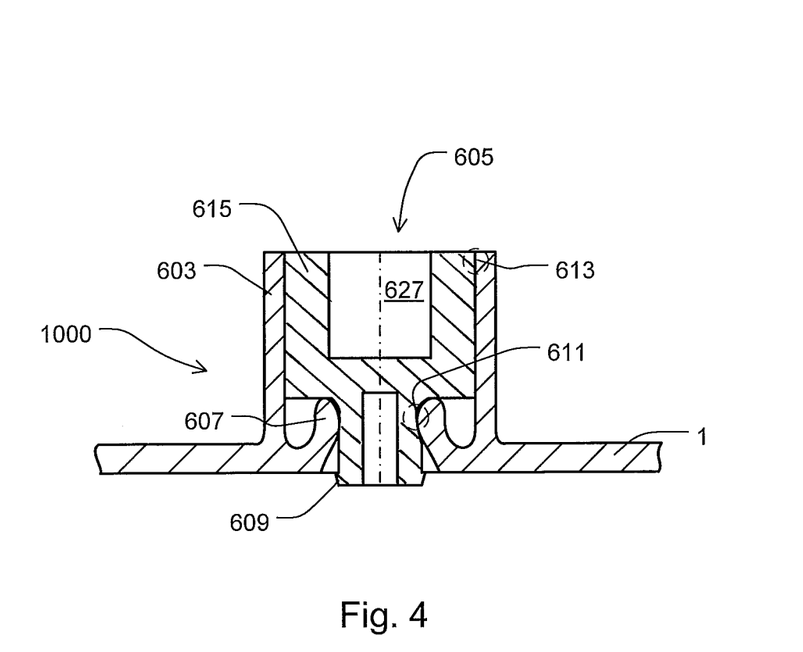
FIG. 4 shows the sterilization opening with the closure device of FIG. 3 in the second closed position.

FIG. 4 shows the sterilization opening 601 in the second, closed position. The latching device 607 which is purely optional is latched. To this end, as shown here by way of example, at least one elastic or non-elastic element which is arranged, for example, circularly or intermittently around a circumference, intrudes a, for example, circularly conducted recess of the closure device 605. Alternatively or in addition an elastic protrusion 609 of the closure device 605 circularly or otherwise engages behind a section of the hard part 1, for example an opening of the sterilization opening 601, or is braced behind the latter.

For the skilled person, it is recognizable that the present invention encompasses also embodiments in which the hard part 1 has an elastic protrusion which engages a section of the closure device 605 or is braced behind the latter.

The latching advantageously ensures that the closure device 605 does not move inadvertently or unintentionally from the second position back to the first position. This may advantageously serve for a safe use of the cassette 1000.

Transferring the closure device 605 into the second position initiates that at least one preliminary sealing surface pairing 611 and/or, optionally, also a second sealing surface pairing 613 come into contact or into engagement with one another. Through such contact or engagement a sealing of the closure device 605 is initiated relative to the hard part 1, here for example relative to the latching device 607 on one hand side and relative to the cylindrical section 603 on the other hand.

Figure 5:
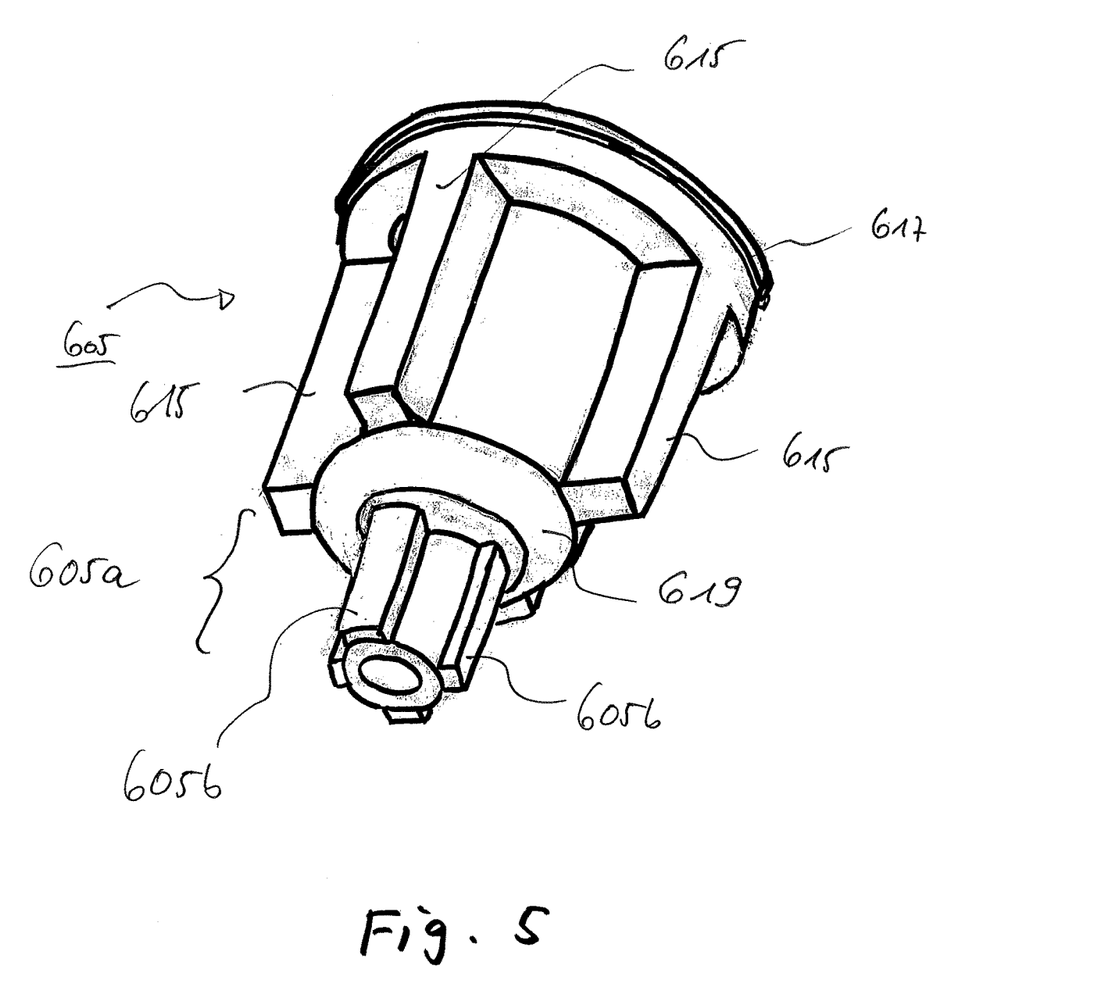
FIG. 5 shows the closure device of FIGS. 3 and 4 in a perspective view.

FIG. 5 shows the closure device 605 of FIGS. 3 and 4 in perspective view.

It can be seen that the closure device 605 is embodied with struts 615 extending in longitudinal extent of the closure device 605 along its circumference (that is, in a direction perpendicular to that plane in which the circumference is located). Through them or past them or alongside of them a permeability is given to the sterilizing fluid. The permeability is then canceled or prevented when an upper ring section 617 and/or a lower ring section 619 suitably come into abutment on sections of the hard part 1 as shown in FIG. 4.

The closure device 605 may have an elastic protrusion 609, as shown in FIG. 4, although this is not shown in FIG. 5. Such a protrusion 609 is optional.

Figure 6:
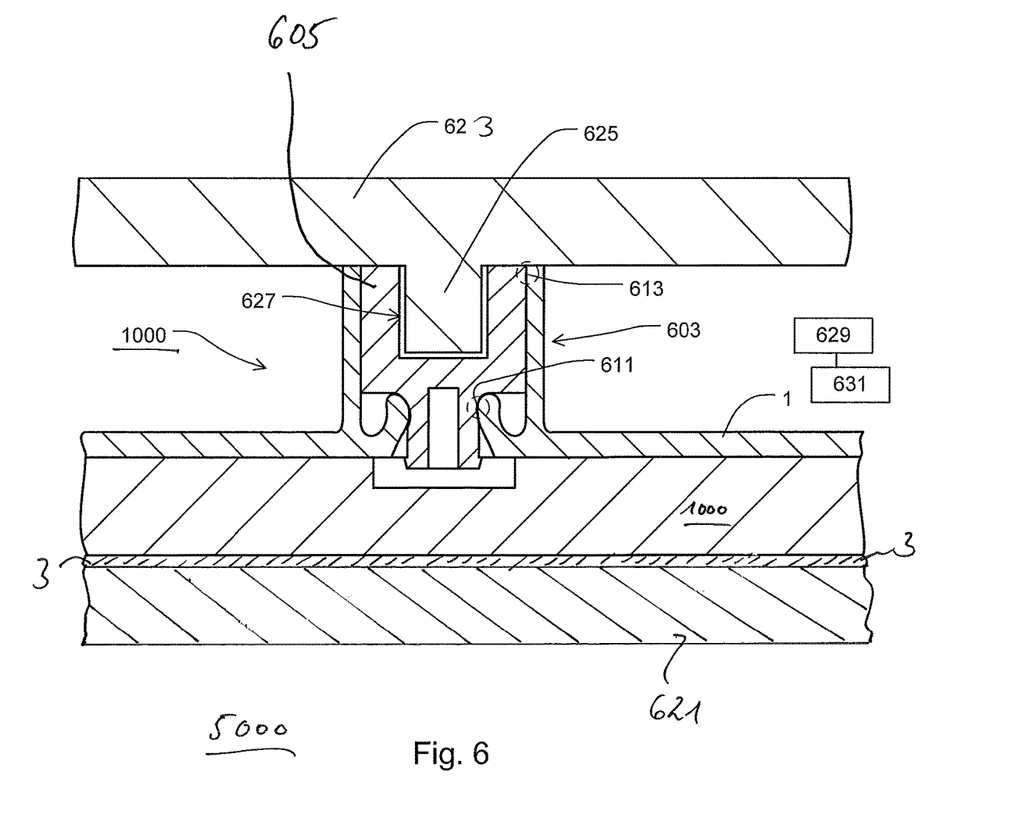
FIG. 6 shows an actuator-sensor mat of an actuator-sensor surface and a machine door of a schematically simplified section of a blood treatment apparatus according to the present invention.

FIG. 6 shows an actuator-sensor mat 621 of an actuator-sensor unit and a machine door 623 of a schematically simplified section of a blood treatment apparatus 5000 according to the present invention.

Between the actuator-sensor mat 621 and the machine door 623 a cassette 1000 is pressed which is indicated only through its hard part 1 with the sterilization opening 601, its cylindrical section 603 and its closure device 605.

An actuator connected to the machine door 623 or plunged through the latter is inserted into a recess or an intrusion 627 of the closure device 605. In the example of FIG. 6, it is the actuator 625 that transferred the closure device 605 into the second, closed position shown in FIG. 6.

In the example of FIG. 6, the actuator 625 is passive, i.e., not actively insertable into the intrusion 627 by hydraulic, mechanical or other means. Rather, it is, at least as far as the actuator 625 as such is concerned, brought sufficiently deep into the intrusion 627 by closing the machine door 623 or the cassette 1000 is pushed sufficiently wide on it by closing the machine door 623. Herein, this will be referred to as passive for the differentiation with respect to an actuator, which is shifted by means of electro-mechanics, pneumatics, mechanics or other means relative to its immediate environment such as the machine door or the actuator-sensor mat with which it is connected respectively.

The sterilization opening 601 in FIG. 6, as well as in FIG. 4, however unlike in FIG. 3, is closed and therefore neither recognizable as opening in the true sense of the word nor provided with a reference numeral in FIG. 4 or in FIG. 6. The location of the sterilization opening 601 may, for example in comparison with FIG. 3, but also in FIG. 4 or FIG. 6, be determined without any effort.

A sensor 629 may be provided to document a transition of the closure device 605 into the second position that had taken place. For this purpose, the sensor 629 may be embodied and utilized as a motion sensor, touch sensor, pressure sensor, optical sensor or the like.

A corresponding signal of the sensor 629 may be applied to a controlling device 631 of the blood treatment apparatus 5000. It may be programmed or configured to only permit a treatment of a patient by means of the blood treatment apparatus 5000, when it is determined by means of sensor 629 that the closure device 605 has been brought into the second position, or it is in any case no longer in the first position.

The invention claimed is:

1. A blood treatment cassette, comprising:
   a cassette body comprising at least a hard part and a film,
   wherein the film is connected to the hard part and at least partially covers the hard part, the hard part defining at least one sterilization opening; and at least one closure device that is connectable to the hard part at the sterilization opening, wherein the closure device is transferrable between a first position relative to the sterilization opening and a second position relative to the sterilization opening, wherein, in the first position, the closure device allows a fluid exchange between an interior and an exterior of the blood treatment cassette through the sterilization opening, wherein, in the second position, the closure device prevents the fluid exchange between the interior and the exterior of the blood treatment cassette through the sterilization opening, and wherein, when the closure device is in the second position, the closure device is irreversibly latched in the second position.

2. The blood treatment cassette according to claim 1, wherein the closure device comprises a mechanism configured to maintain the closure device irreversibly latched in the second position.

3. The blood treatment cassette according to claim 2, wherein the mechanism comprises a latching device.

4. The blood treatment cassette according to claim 1, wherein the closure device comprises at least two sealing surface pairings, sealing sections or sealing elements.

5. A blood treatment apparatus configured to be connectable to the blood treatment cassette according to claim 1, wherein the blood treatment apparatus comprises:

an actuator configured to interact with the closure device of the blood treatment cassette and transfer the closure device from the first position to the second position.

6. A blood treatment apparatus connected to the blood treatment cassette according to claim 1, wherein the blood treatment apparatus comprises:

an actuator configured to interact with the closure device of the blood treatment cassette and transfer the closure device from the first position to the second position.

7. A blood treatment apparatus connected to the blood treatment cassette according to claim 2, wherein the blood treatment apparatus comprises:

an actuator configured to interact with the closure device of the blood treatment cassette and transfer the closure device from the first position to the second position.

8. The blood treatment apparatus according to claim 5, wherein the actuator is a passive actuator comprising a fixed protruding member configured in or on an actuator-sensor-mat, a machine door or an actuator-sensor-plate.

9. The blood treatment apparatus according to claim 5, further comprising a device which is configured to change the actuator or at least one property of the actuator, or to transfer the closure device by means of the actuator from the first position into the second position.

10. The blood treatment apparatus according to claim 6, further comprising a device which is configured to change the actuator or at least one property of the actuator, or to transfer the closure device by means of the actuator from the first position into the second position.

11. The blood treatment apparatus according to claim 7, further comprising a control device and at least one sensor,
wherein the blood treatment apparatus is configured to determine by means of the at least one sensor whether the closure device is in the second position, and
wherein the blood treatment apparatus is further configured to prevent or interrupt a blood treatment upon the determination by the blood treatment apparatus or the at least one sensor that the closure device is not in the second position.

12. The blood treatment apparatus according to claim 8, further comprising a control device and at least one sensor,
wherein the blood treatment apparatus is configured to determine by means of the at least one sensor whether the closure device is in the second position, and
wherein the blood treatment apparatus is further configured to prevent or interrupt a blood treatment upon the determination by the blood treatment apparatus or the at least one sensor that the closure device is not in the second position.

13. The blood treatment apparatus according to claim 9, further comprising a control device and at least one sensor,
wherein the blood treatment apparatus is configured to determine by means of the at least one sensor whether the closure device is in the second position, and
wherein the blood treatment apparatus is further configured to prevent or interrupt a blood treatment upon the determination by the blood treatment apparatus or the at least one sensor that the closure device is not in the second position.

* * * * *